United States Patent
Matsuura et al.

(10) Patent No.: US 11,492,322 B2
(45) Date of Patent: Nov. 8, 2022

(54) METHOD FOR PRODUCING FLUORINATED COMPOUND

(71) Applicants: DAIKIN INDUSTRIES, LTD., Osaka (JP); UNIVERSITY PUBLIC CORPORATION OSAKA, Osaka (JP)

(72) Inventors: Makoto Matsuura, Osaka (JP); Yoshichika Kuroki, Osaka (JP); Yosuke Kishikawa, Osaka (JP); Ilhyong Ryu, Osaka (JP); Takahide Fukuyama, Osaka (JP)

(73) Assignees: DAIKIN INDUSTRIES, LTD., Osaka (JP); UNIVERSITY PUBLIC CORPORATION OSAKA, Osaka (JP)

( * ) Notice: Subject to any disclaimer, the term of this patent is extended or adjusted under 35 U.S.C. 154(b) by 30 days.

(21) Appl. No.: 17/254,437

(22) PCT Filed: Jun. 20, 2019

(86) PCT No.: PCT/JP2019/024610
§ 371 (c)(1),
(2) Date: Dec. 21, 2020

(87) PCT Pub. No.: WO2019/245008
PCT Pub. Date: Dec. 26, 2019

(65) Prior Publication Data
US 2021/0221766 A1     Jul. 22, 2021

(30) Foreign Application Priority Data
Jun. 22, 2018     (JP) .............................. JP2018-119223

(51) Int. Cl.
*C07C 67/347* (2006.01)
*B01J 31/18* (2006.01)
(Continued)

(52) U.S. Cl.
CPC ......... *C07C 67/347* (2013.01); *B01J 31/1815* (2013.01); *C07C 37/62* (2013.01);
(Continued)

(58) Field of Classification Search
CPC ............ B01J 2231/4294; B01J 2231/44; B01J 2531/821; B01J 2531/827; B01J 31/1815;
(Continued)

(56) References Cited

U.S. PATENT DOCUMENTS

| 5,017,718 A | 5/1991 | Ojima et al. |
| 2005/0283032 A1 | 12/2005 | Curran et al. |
| 2019/0071376 A1 | 3/2019 | Matsuura et al. |

FOREIGN PATENT DOCUMENTS

| JP | 9-67323 | 3/1997 | |
| WO | 2017/154948 | 9/2017 | |
| WO | WO-2017154948 A1 * | 9/2017 | ............. C07B 37/04 |

OTHER PUBLICATIONS

Liu et al. (2-Difluoromethylene-4-methylenepentanoic Acid, a Paradoxial Probe Able to Mimic the Signaling Role of 2-Oxoglutaric Acid in Cyanobacteria, Organic Letters, vol. 13(11), pp. 2924-2927, Published 2011) (Year: 2011).*

(Continued)

*Primary Examiner* — Yevgeny Valenrod
*Assistant Examiner* — Blaine G Doletski
(74) *Attorney, Agent, or Firm* — Wenderoth, Lind & Ponack, L.L.P.

(57) ABSTRACT

An object of the present invention is to provide a novel method for producing a fluorine-containing methylene compound. The above object can be achieved by a method for producing a compound represented by formula (1):

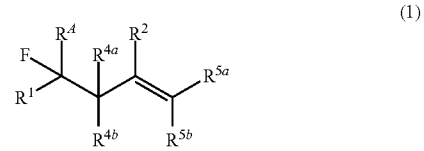

wherein $R^1$ represents an organic group, $R^A$ represents hydrogen or fluorine, $R^{4a}$ represents hydrogen or an organic group, $R^{4b}$ represents hydrogen or an organic group, $R^{5a}$ represents hydrogen or an organic group, $R^{5b}$ represents hydrogen or an organic group, and
$R^2$ represents hydrogen or an organic group; $R^2$ is optionally connected to $R^{4a}$ to form a ring; the method comprising step A of reacting a compound represented by formula (2):

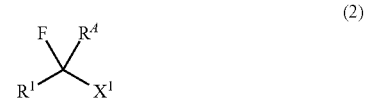

wherein $X^1$ represents a leaving group, and other symbols are as defined above, with a compound represented by formula (3):

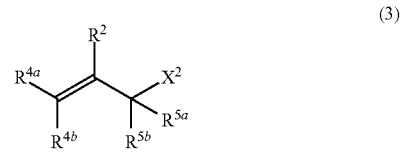

(Continued)

wherein $X^2$ represents a leaving group, and other symbols are as defined above, in the presence of a reducing agent as desired, under light irradiation.

15 Claims, No Drawings

(51) Int. Cl.
*C07C 37/62* (2006.01)
*C07C 67/343* (2006.01)
(52) U.S. Cl.
CPC ..... *C07C 67/343* (2013.01); *B01J 2231/4294* (2013.01); *B01J 2531/821* (2013.01)
(58) Field of Classification Search
CPC ... C07B 2200/07; C07C 17/263; C07C 21/18; C07C 22/08; C07C 231/12; C07C 233/09; C07C 37/62; C07C 67/343; C07C 67/347; C07C 69/593; C07C 69/65
See application file for complete search history.

(56) References Cited

OTHER PUBLICATIONS

International Search Report dated Sep. 10, 2019 in corresponding International (PCT) Application No. PCT/JP2019/024610.
John T. Welch et al., "Advances in the Preparation of Biologically Active Organofluorine Compounds", Tetrahedron, 1987, vol. 43, No. 14, p. 3123.
Brandange et al., "Highly Selective re Additions to a Masked Oxaloacetate Absolute Configurations of Fluorocitric Acids", Journal of the American Chemical Society, 1981, vol. 103, pp. 4452-4458.
Kosobokov et al., "Geminal Silicon/Zinc Reagent as an Equivalent of Difluoromethylene Bis-carbanion", Organic Letters, 2014, vol. 16, pp. 1438-1441.
Sato et al., "Reactions of ethyl bromodifluoroacetate in the presence of copper powder", Journal of Fluorine Chemistry, 2004, vol. 125, pp. 509-515.
Si et al., "An efficient synthesis of 3,4-dihydropyridone via a tandem olefin isemerization-ring-closing metathesis reaction", Tetrahedron Letters, 2014, vol. 55, pp. 5529-5532.
Sumino et al., "Photoredox-Catalyzed Hydrodifluoroalkylation of Alkenes Using Difluorohaloalkyl Compounds and a Hantzsch Ester", The Journal of Organic Chemistry, 2017, vol. 82, pp. 5469-5474.
Sumino et al., "Palladium/Light Induced Radical Alkenylation and Allylation of Alkyl Iodides Using Alkenyl and Allylic Sulfones", Organic Letters, Feb. 2018, vol. 20, pp. 1078-1081.
Heitz et al., "Visible-light-Mediated Alkenylation, Allylation, and Cyanation of Potassium Alkyltrifluoroborates with Organics Photoredox Catalysts", The Jounal of Organic Chemistry, 2016, vol. 81, pp. 7308-7313.
Napoli, M. et al., "Effects of the reaction conditions on 3-(perfluorohexyl)prop-l-ene formation from perfluorohexyl iodide and allyl chloride", Journal of Fluorine Chemistry, 2001, vol. 111, pp. 49-59.
Myers, Andrew G. et al., "Practical Methodology for the Asymmetric Synthesis of Organofluorine Compounds", Tetrahedron Letters, 1998, vol. 39, pp. 1335-1338.
Chen, L.F. et al., "Iodofluoroalkylsulfonyl Fluorides—Synthesis and Conversion to New Derivaiives", Journal of Fluorine Chemistry, 1989, vol. 43, pp. 329-347.
Extended European Search Report dated Feb. 16, 2022 in corresponding European Patent Application No. 19823150.8.
Yajima, Tomoko et al., "Photoinduced addition and addition-elimination reactions of perfluoroalkyl iodides to electron-deficient olefins", Tetrahedron, 2012, vol. 68, No. 34, pp. 6856-6861.
Haszeldine, Robert N. et al.,"Fluoro-olefin Chemistry. Part 15.[1] Thermal Reaction of Hexafluoropropene with Hydrocarbon Olefins", Journal of the Chemical Society, Perkin Transactions 1, 1982, p. 2219.
Rawner, Thomas et al., "The Different Faces of Photoredox Catalysts: Visible-light-Mediated Atom Transfer Radical Addition (ATRA) Reactions of Perfluoroalkyl Iodides with Styrenes and Phenylacetylenes", ACS Catalysis, 2018, vol. 8, No. 5, pp. 3950-3956.
Yoshida, Masato et al., "Convenient preparation of difluoromethylene-functionalized compounds from chlorodifluoroacetic acid", Journal of Fluorine Chemistry, 1994, vol. 68, No. 1, pp. 33-38.
Liu, Xinjun et al., "2-Difluoromethylene-4-methylenepentanoic Acid, a Paradoxical Probe Able to Mimic the Signaling Role of 2-Oxoglutaric Acid in Cyanobacteria", Organic Letters, 2011, vol. 13, No. 11, pp. 2924-2927.
Alvey, Luke J. et al., "Additions of $PH_3$ to Monosubstituted Alkenes of the Formula $H_2C=CH(CH_2)_x(CF_2)_xCF_3$ : Convenient, Multigram Syntheses of a Family of Partially Fluorinated Trialkylphosphines with Modulated Electronic Properties and Fluorous Phase Affinities", The Journal of Organic Chemistiy, American Chemical Society, 1998, vol. 63, pp. 6302-6308.
Yu, Wei et al., "Visible Light-induced Methoxycarbonyldifluoromethylation of Trimethylsilyl Enol Ethers and Allyltrimethylsilanes with $FSO_2CF_2CO_2Me$", Chinese Journal of Chemistry, 2018, vol. 36, No. 11, pp. 1024-1030.
Liang, Hui et al., "Dual Catalytic Switchable Divergent Synthesis: an Asymmetric Visible-light Photocatalytic Approach to Fluorine-Containing γ-Keto Acid Frameworks", The Journal of Organic Chemistry, 2019, vol. 84, No. 1, pp. 60-72.

* cited by examiner

METHOD FOR PRODUCING FLUORINATED COMPOUND

TECHNICAL FIELD

The present invention relates to a method for producing a fluorine-containing compound.

BACKGROUND ART

Since some physiologically active substances in vivo are fluorinated methylene-containing compounds, applications of fluoromethylene-containing compounds to, e.g., drugs have been actively studied.

For example, methods for producing fluorine-containing methylene compounds, such as α-fluoromethylene compounds and α-difluoroaldol compounds, which are carbonyl compounds having, at the α-position, at least one substituent selected from the group consisting of fluorine atoms and perfluoro organic groups, are highly useful (Non-patent Literature 1 and 2).

As one example of the method for producing a fluorine-containing methylene compound, Patent Literature 1 discloses the following.

A method for producing a compound represented by formula (1) or a ring-closed or ring-open derivative of the compound:

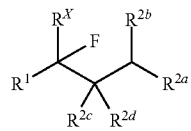

(1)

wherein $R^1$ represents an organic group,
$R^X$ represents hydrogen or fluorine,
$R^{2a}$, $R^{2b}$, $R^{2c}$, and $R^{2d}$ are the same or different, and each represents $-Y-R^{21}$ or $-N(-R^{22})_2$, or $R^{2b}$ may be connected to $R^{2c}$ to form a bond,
wherein Y represents a bond, oxygen, or sulfur,
$R^{21}$ represents hydrogen or an organic group, and
$R^{22}$, in each occurrence, is the same or different, and represents hydrogen or an organic group;
the method comprising step A of reacting a compound represented by the following formula (2):

(2)

wherein X represents a leaving group, and other symbols are as defined above,
with a compound represented by the following formula (3):

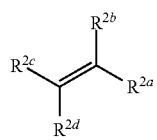

(3)

wherein the symbols are as defined above,
in the presence of a reducing agent under light irradiation.

CITATION LIST

Patent Literature

PTL 1: Pamphlet of WO2017/154948

Non-Patent Literature

NPL 1: John T. Welch et al., Tetrahedron, 1987, 43, 14, p. 3123
NPL 2: Svante et al., J. Am. Chem. Soc., 1981, 103, p. 4452

SUMMARY OF INVENTION

Technical Problem

However, another novel method for producing a fluorine-containing methylene compound is desired.

The present disclosure aims to provide a novel method for producing a fluorine-containing methylene compound.

Solution to Problem

The present disclosure includes the following embodiments.

Item 1. A method for producing a compound represented by formula (1)

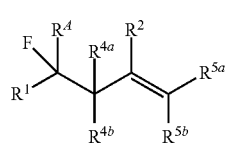

(1)

wherein $R^1$ represents an organic group,
$R^A$ represents hydrogen or fluorine,
$R^{4a}$ represents hydrogen or an organic group,
$R^{4b}$ represents hydrogen or an organic group,
$R^2$ represents hydrogen or an organic group,
$R^{5a}$ represents hydrogen or an organic group, and
$R^{5b}$ represents hydrogen or an organic group; or
$R^2$ is optionally connected to $R^{4a}$ to form a ring;
the method comprising step A of reacting a compound represented by formula (2):

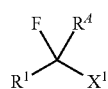

(2)

wherein $X^1$ represents a leaving group, and other symbols are as defined above,
with a compound represented by formula (3):

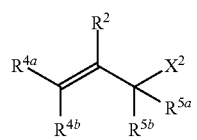

(3)

wherein $X^2$ represents a leaving group, and other symbols are as defined above,
in the presence of a reducing agent as desired, under light irradiation.

Item 2. The production method according to Item 1, wherein
$R^1$ represents $R^{11}$—Y— or $(R^{11}$—$)_2$N—,
Y represents a bond, oxygen, or sulfur, and
$R^{11}$ independently represents, in each occurrence, a hydrocarbon group that optionally has one or more substituents.

Item 3. The production method according to Item 2, wherein
$R^1$ represents $R^{11}$—Y—,
Y represents a bond, and
$R^{11}$ represents
an aryl group that optionally has one or more substituents, or
an alkyl group that optionally has one or more substituents.

Item 4.
The production method according to Item 2, wherein
$R^1$ represents $R^{11}$—Y—,
Y represents —O—C(=O)— or —O—C(=S)—, and
$R^{11}$ represents an aliphatic hydrocarbon group that optionally has one or more substituents.

Item 5.
The production method according to Item 2, wherein
$R^1$ represents $(R^{11}$—$)_2$N—C(=O)— and
$R^{11}$ independently represents, in each occurrence, an aliphatic hydrocarbon group that optionally has one or more substituents.

P Item 6
The production method according to any one of Item 1 to 5, wherein $R^4$ represents fluorine.

Item 7.
The production method according to any one of Items 1 to 6, wherein
$R^{4a}$ represents hydrogen,
$R^{4b}$ represents hydrogen,
$R^2$ represents hydrogen,
a hydrocarbon group that optionally has one or more substituents,
or
an alkoxycarbonyl group that optionally has one or more substituents,
$R^{5a}$ represents hydrogen, and
$R^{5b}$ represents hydrogen.

Item 8.
The production method according to any one of Items 1 to 7, wherein
$X^1$ represents
halogen,
an alkylsulfonyloxy group, or
an arylsulfonyloxy group.

Item 9.
The production method according to any one of Items 1 to 8, wherein
$X^2$ represents
—$SO_2R$,
—SR,
—S(=O)R,
—SeR,
—TeR,
—Cl
—Br,
—$PR_2$, or
—P(=O)$R_2$,
wherein R independently represents, in each occurrence, an organic group.

Item 10.
The production method according to Item 9, wherein $X^2$ represents —$SO_2R$, wherein R is an organic group.

Item 11.
The production method according to any one of Items 1 to 10, wherein the reducing agent is a nitrogen-containing unsaturated heterocyclic compound having an N—H moiety.

Item 12.
The production method according to any one of Items 1 to 11, wherein the reducing agent is a compound represented by formula (4):

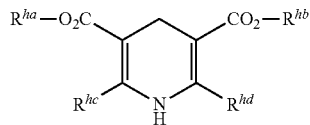

wherein $R^{ha}$, $R^{hb}$, $R^{hc}$, and $R^{hd}$ are the same or different, and each represents alkyl.

Item 13.
The production method according to any one of Items 1 to 12, wherein the reaction of step A is performed in the presence of a catalyst.

Item 14.
The production method according to Item 13, wherein the catalyst is at least one member selected from the group consisting of transition metal complexes and organic dye compounds.

Item 15.
A method for producing a compound represented by formula (1a):

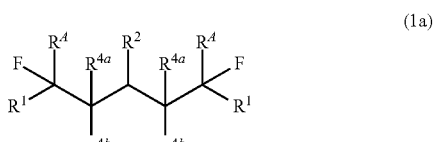

wherein
$R^1$ independently represents, in each occurrence, an organic group,
$R^4$ independently represents, in each occurrence, hydrogen or fluorine,
$R^{4a}$ independently represents, in each occurrence, hydrogen or an organic group,
$R^{4b}$ independently represents, in each occurrence, hydrogen or an organic group, and
$R^2$ represents hydrogen or an organic group;
the method comprising step Aa of reacting a compound represented by formula (2):

wherein $X^1$ represents a leaving group, and other symbols are as defined above, with a compound represented by formula (3):

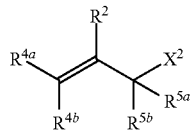

wherein $X^2$ represents a leaving group, and other symbols are as defined above,
in the presence of a reducing agent as desired, under light irradiation.
Item 16.
A compound represented by formula (1):

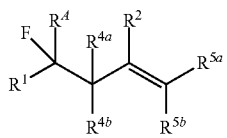

wherein R represents an organic group,
$R^A$ represents hydrogen or fluorine,
$R^{4a}$ represents hydrogen or an organic group,
$R^{4b}$ represents hydrogen or an organic group,
$R^2$ represents an organic group,
$R^{5a}$ represents hydrogen or an organic group, and
$R^{5b}$ represents hydrogen or an organic group, with the proviso that
when $R^1$ represents a perfluoroalkyl group, $R^2$ represents an alkyl group having two or more carbon atoms, or an ester group having three or more carbon atoms.
Item 17.
The compound according to Item 16,
wherein
$R^1$ represents $R^{11}$—Y—,
Y represents a bond,
$R^{11}$ represents an aryl group that optionally has one or more substituents, or an alkyl group that optionally has one or more substituents,
represents hydrogen or fluorine, and
$R^2$ represents hydrogen or an organic group.
Item 18.
The compound according to Item 17, wherein $R^A$ represents fluorine.
Item 19.
The compound according to Item 17 or 18,
wherein
$R^{4a}$ represents hydrogen,
$R^{4b}$ represents hydrogen,
$R^2$ represents hydrogen,
an alkoxycarbonyl group that optionally has one or more substituents,
an aryl group that optionally has one or more substituents, or
an alkyl group that optionally has one or more substituents,
$R^{5a}$ represents hydrogen, and
$R^{5b}$ represents hydrogen.
Item 20.
The compound according to Item 16, wherein
$R^1$ represents $R^{11}$—Y—,
Y represents —O—C(=O)— or —O—C(=S)—,
$R^{11}$ represents an aliphatic hydrocarbon group that optionally has one or more substituents,
$R^A$ represents hydrogen or fluorine, and
$R^2$ represents hydrogen or an organic group.
Item 21.
The compound according to Item 20, wherein $R^A$ represents fluorine.
Item 22.
The compound according to Item 20 or 21,
wherein
$R^{4a}$ represents hydrogen,
$R^{4b}$ represents hydrogen,
$R^2$ represents hydrogen, an alkoxycarbonyl group that optionally has one or more substituents, an aryl group that optionally has one or more substituents, or an alkyl group that optionally has one or more substituents,
$R^{5a}$ represents hydrogen, and
$R^{5b}$ represents hydrogen.
Item 23.
The compound according to Item 16,
wherein
$R^1$ represents $R^{11}$—Y—,
Y represents —O—C(—O—)— or —O—C(=S)—,
$R^{11}$ represents an aliphatic hydrocarbon group that optionally has one or more substituents,
$R^A$ represents hydrogen or fluorine, and
$R^2$ represents hydrogen or an organic group.
Item 24.
The compound according to Item 16,
wherein
$R^1$ represents $(R^{11}—)_2N—C(—O—)—$,
$R^{11}$ independently represents, in each occurrence, an aliphatic hydrocarbon group that optionally has one or more substituents,
$R^A$ represents hydrogen or fluorine,
$R^{4a}$ represents hydrogen,
$R^{4b}$ represents hydrogen,
$R^2$ represents hydrogen or an organic group,
$R^{5a}$ represents hydrogen, and
$R^{5b}$ represents hydrogen or an organic group.
Item 25.
The compound according to Item 24, wherein R represents fluorine.

Advantageous Effects of Invention

The present disclosure provides an efficient, novel method for producing a compound having a fluoromethylene group.

DESCRIPTION OF EMBODIMENTS

Terms

The symbols and the abbreviations in this specification are to be interpreted as having the general meanings in the related technical field to which the present disclosure pertains, according to the context of this specification, unless otherwise specified.

In this specification, the terms "comprise" and "contain" encompass the meanings of consisting essentially of and consisting of.

The steps, treatments, or operations in this specification can be performed at room temperature unless otherwise specified.

In this specification, room temperature refers to a temperature in a range of 10 to 40° C.

In this specification, "$C_{n-m}$" (herein, n and m are each natural numbers) indicates that the carbon number is n or more and m or less, as conventionally used in the field of organic chemistry.

In this specification, the term "fluoromethylene" includes monofluoromethylene and difluoro methylene unless otherwise specified.

In this specification, unless otherwise specified, examples of "halogen atom" include fluorine, chlorine, bromine, and iodine.

In this specification, unless otherwise specified, the term "organic group" refers to a group containing at least one carbon atom as its constituent atom.

In this specification, unless otherwise specified, examples of "organic group" include hydrocarbon, cyano, carboxy, alkoxy, ester, ether, and acyl.

In this specification, unless otherwise specified, the term "hydrocarbon" refers to a group containing at least one carbon atom and at least one hydrogen atom as its constituent atoms.

In this specification, unless otherwise specified, examples of "hydrocarbon" include aliphatic hydrocarbon, aromatic hydrocarbon (aryl), and combinations thereof.

In this specification, unless otherwise specified, the term "aliphatic hydrocarbon" may be linear, branched, or cyclic aliphatic hydrocarbon, or a combination thereof.

In this specification, unless otherwise specified, the term "aliphatic hydrocarbon" may be saturated or unsaturated aliphatic hydrocarbon.

In this specification, unless otherwise specified, examples of "aliphatic hydrocarbon" include alkyl, alkenyl, alkynyl, and cycloalkyl.

In this specification, unless otherwise specified, the term "alkyl" refers to, for example, linear or branched, primary, secondary, or tertiary $C_{1-15}$ alkyl (e.g., $C_{1-12}$ alkyl and $C_{1-10}$ alkyl), such as methyl, ethyl, propyl (e.g., n-propyl and isopropyl), butyl (n-butyl, isobutyl, sec-butyl, tert-butyl), pentyl (e.g., n-pentyl, tert-pentyl, neopentyl, isopentyl, sec-pentyl, and 3-pentyl), hexyl, heptyl, octyl, nonyl, and decyl.

In this specification, the term "fluoroalkyl" refers to alkyl having at least one hydrogen atom replaced by a fluorine atom.

In this specification, the number of fluorine atoms in the "fluoroalkyl" may be one or more (e.g., 1 to 3, 1 to 6, 1 to 12, or 1 to the maximum replaceable number).

The term "fluoroalkyl" includes perfluoroalkyl. The term "perfluoroalkyl" refers to alkyl having all hydrogen atoms replaced by fluorine atoms.

In this specification, unless otherwise specified, the term "alkenyl" refers to, for example, linear or branched $C_{1-10}$ alkenyl, such as vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

In this specification, unless otherwise specified, the term "alkynyl" refers to, for example, linear or branched $C_{2-6}$ alkynyl, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

In this specification, unless otherwise specified, the term "cycloalkyl" refers to, for example, $C_{3-10}$ cycloalkyl (preferably $C_{4-10}$ cycloalkyl), such as cyclopentyl, cyclohexyl, and cycloheptyl.

In this specification, unless otherwise specified, the term "alkoxy" refers to, for example, a group represented by RO— (wherein R represents alkyl).

In this specification, unless otherwise specified, the term "ester" refers to, for example, a group represented by formula $RCO_2$— (wherein R represents alkyl).

In this specification, unless otherwise specified, the term "ether" refers to a group having an ether bond (—O—) and examples of ether include polyether. Examples of polyether include groups represented by formula $R^a$—(O—$R^b$)$_n$— (wherein $R^a$ represents alkyl, $R^b$, in each occurrence, is the same or different, and represents alkylene, and n is an integer of 1 or more). Alkylene is a divalent group formed by removing one hydrogen atom from the alkyl group.

In this specification, unless otherwise specified, the term "acyl" includes alkanoyl. In this specification, unless otherwise specified, the term "alkanoyl" refers to, for example, a group represented by RCO— (wherein R represents alkyl).

In this specification, unless otherwise specified, the term "aromatic group" includes aryl and heteroaryl.

In this specification, examples of "aryl" include $C_{6-14}$ aryl (e.g., $C_{6-10}$ aryl), such as phenyl and naphthyl.

In this specification, examples of "heteroaryl" include 5- to 14-membered (monocyclic, dicyclic, or tricyclic) heterocyclic groups containing, in addition to carbon, 1 to 4 heteroatoms selected from the group consisting of nitrogen, sulfur, and oxygen as an annular atom.

In this specification, examples of "heteroaryl" include (1) monocyclic aromatic heterocyclic groups, such as furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl, and triazinyl; and (2) polycyclic (e.g., dicyclic) aromatic heterocyclic groups, such as quinolyl, isoquinolyl, quinazolvl, quinoxalyl, benzofuryl, benzothienyl, benzoxazolyl, benzisoxazolyl, benzothiazolyl, benzimidazolyl, benzotriazolyl, indolyl, indazolyl, pyrrolo pyrazinyl, imidazo pvridinyl, imidazo pyrazinyl, imidazo thiazolyl pyrazolo pyridinyl, pyrazolo thienyl, and pvrazolo thoriadinyl.

In the specification, examples of "aromatic rings" include (1) aromatic carbon rings such as a benzene ring and a naphthalene ring, and (2) 5- or 6-membered monocyclic aromatic heterocyclic rings having as the ring-constituting atoms, in addition to carbon atoms, 1 to 3 heteroatoms selected from oxygen, sulfur, and nitrogen. Specific examples of such 5- or 6-membered monocyclic aromatic heterocyclic rings include a furan ring, a thiophene ring, a pyrrole ring, an oxazole ring, an isoxazol ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring, a triazine ring, and the like.

In this specification, examples of a "non-aromatic hydrocarbon ring" include $C_{3-8}$ non-aromatic hydrocarbon rings. Specific examples include:

(1) $C_{3-8}$ cycloalkanes, such as cyclopropane, cyclobutane, cyclopentane, cyclohexane, cycloheptene, and cyclooctane;

(2) $C_{5-8}$ cycloalkenes, such as cyclopentene, cyclohexene, cycloheptene, and cyclooctene;

(3) $C_{5-8}$ cycloalkadienes, such as cyclopentadiene, cyclohexadiene, cycloheptadiene, and cyclooctadiene; and (4) $C_{5-8}$ bridged-ring hydrocarbons, such as bicyclo[2.1.0]pentane, bicyclo[2.2.1]heptane, bicyclo[3.2.1]octane, bicyclo[2.2.1]hept-2-ene, and tricyclo[2.2.1.0]heptane.

In this specification, examples of "non-aromatic heterocyclic rings" include 3- to 8-membered non-aromatic heterocyclic rings and the like. Specific examples include oxirane, azetidine, oxetane, thietane, pyrrolidine, dihydrofuran, tetrahydrofuran, tetrahydrothiophene, imidazolidine, cxazolidine, isoxazoline, piperidine, dihydropyran, tetrahydropyran, tetrahydrothiopyran, morpholine, thiomorpholine, piperazine, dihydrooxazine, tetrahydrooxazine, dihydropyrimidine, tetrahydropyrimidine, azepane, oxepane, thiepane, oxazepane, thiazepane, azocane, oxocane, thiocane, oxazocane, and thiazocane.

Production Method: Compound (1)

The method for producing a compound represented by formula (1) (in the specification, sometimes referred to as "compound (1)"):

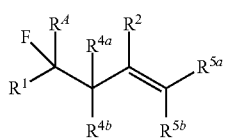
(1)

wherein $R^1$ represents an organic group,
$R^A$ represents hydrogen or fluorine,
$R^{4a}$ represents hydrogen or an organic group,
$R^{4b}$ represents hydrogen or an organic group,
$R^{5a}$ represents hydrogen or an organic group,
$R^{5b}$ represents hydrogen or an organic group, and
$R^2$ represents hydrogen or an organic group; or
$R^2$ may be connected to $R^{4a}$ to form a ring;
the method comprising step A of reacting a compound represented by formula (2):

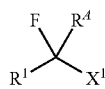
(2)

wherein $X^1$ represents a leaving group, and other symbols are as defined above,
with a compound represented by formula (3):

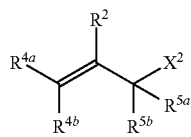
(3)

wherein $X^2$ represents a leaving group, and other symbols are as defined above,
in the presence of a reducing agent as desired under light irradiation.

In one preferable embodiment of the present invention,
$R^1$ represents $R^{11}$—Y— or $(R^{11}$—$)_2$N—,
Y represents a bond, oxygen, or sulfur, and
$R^{11}$ independently represents, in each occurrence, a hydrocarbon group that may have one or more substituents.

In a more preferable embodiment of the present invention,
$R^1$ represents $R^{11}$—Y—,
Y represents a bond, and
$R^{11}$ represents an aryl group that may have one or more substituents, or an alkyl group that may have one or more substituents.
$R^{11}$ preferably represents an aryl group or a perfluoroalkyl group.

In another preferable embodiment of the present invention,
$R^1$ represents $R^{11}$—Y—,
Y represents —O—C(—O—)— or —O—C(=S)—, and
$R^{11}$ represents an aliphatic hydrocarbon group that may have one or more substituents.
$R^{11}$ preferably represents a $C_{1-6}$ alkyl group or a $C_{7-11}$ aralkyl group (e.g., benzyl).

In yet another more preferable embodiment of the present invention,
$R^1$ represents $(R^{11}$—$)_2$N—C(=O)— and
$R^{11}$ independently represents, in each occurrence, a hydrocarbon group that may have one or more substituents.
Preferably, $R^{11}$ independently represents, in each occurrence, $C_{1-6}$ alkyl.

$R^A$ preferably represents fluorine.

xamples of the "ring" formed by connecting $R^2$ to $R^4$ include aromatic rings, non-aromatic hydrocarbon rings, and non-aromatic heterocyclic rings.

Examples of substituents of the ring include halogen, nitro, cyano, amino, hydroxy, carboxy, alkyl, alkenyl, and alkynyl.

$R^2$ preferably represents
hydrogen,
a hydrocarbon group that may have one or more substituents, or
an alkoxycarbonyl group that may have one or more substituents.

$R^2$ more preferably represents
hydrogen,
$C_{1-6}$ alkyl that may have one or more substituents,
$C_{6-14}$ aryl that may have one or more substituents, or
$C_{1-6}$ alkoxy-carbonyl that may have one or more substituents.

$R^{4a}$ preferably represents hydrogen.
$R^{4b}$ preferably represents hydrogen.
$R^{5a}$ preferably represents hydrogen.
$R^{5b}$ preferably represents hydrogen.
$R^2$ preferably represents
hydrogen, a hydrocarbon group that may have one or more substituents, or an alkoxycarbonyl group that may have one or more substituents;
$R^{4a}$ preferably represents hydrogen,
$R^{4b}$ preferably represents hydrogen,
$R^{5a}$ preferably represents hydrogen, and
$R^5$ preferably represents hydrogen.

Examples of the leaving group represented by $X^1$ include halogen (e.g., fluorine, chlorine, bromine, and iodine), alkylsulfonyloxy (e.g., $C_{1-6}$ alkylsulfonyloxy, such as methanesulfonyloxy and trifluoromethanesulfonyloxy); and arylsulfonyloxy (e.g., $C_{6-10}$ arylsulfonyloxy, such as benzene sulfonyloxy and p-toluenesulfonyloxy).

$X^1$ preferably represents halogen, an alkylsulfonyloxy group, or an arylsulfonyloxy group.

$X^2$ preferably represents
—SO$_2$R,
—SR,
—S(=O)R,
—SeR,

—TeR,
—Cl,
—Br,
—I,
—PR$_2$, or
—P(=O)R$_2$,
wherein R independently represents, in each occurrence, an organic group.

X$^2$ more preferably represents —SO$_2$R, wherein R is an organic group.

The amount of compound (3) used in step A is preferably in the range of 1.0 to 20.0 moles, more preferably in the range of 1.3 to 10 moles, and even more preferably in the range of 1.5 to 5 moles, per mole of compound (2).

The reaction of step A is preferably performed as desired in the presence of a reducing agent.

The reducing agent may be an inorganic or organic reducing agent. Examples of the reducing agent include hydrogen, formic acid, ammonium formate, sodium formate, formic acid triethylamine, triethylsilan, tetramethyl disiloxane, polymethylhydrosiloxane, NaBH$_3$CN, NHCBH$_3$ (N-heterocyclic carbene boranes), and a nitrogen-containing unsaturated heterocyclic compound having an N—H moiety (imino group).

Preferable examples of the reducing agent include a nitrogen-containing unsaturated heterocyclic compound having an N—H moiety.

Preferable examples of the "nitrogen-containing unsaturated heterocyclic compound having an N—H moiety" that can be used as a reducing agent include a compound represented by formula (4) (sometimes referred to in this specification as "compound (4)"),

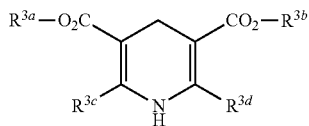

wherein R$^{3a}$, R$^{3b}$, R$^{3c}$, and R$^{3d}$ are the same or different, and each represents alkyl.

R$^{3a}$ preferably represents C$_{1-6}$ alkyl, and more preferably methyl or ethyl.

R$^{3b}$ preferably represents C$_{1-6}$ alkyl, and more preferably methyl or ethyl.

R$^{3c}$ preferably represents C$_{1-6}$ alkyl, and more preferably methyl or ethyl.

R$^{3d}$ preferably represents C$_{1-6}$ alkyl, and more preferably methyl or ethyl.

More preferable examples of the reducing agent that can be used in the present disclosure include compounds represented by the formulae below. These compounds are "Hantzsch esters" (sometimes abbreviated in this specification as "HEH").

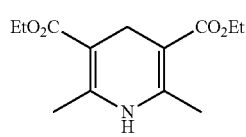

Hantzsch ester a

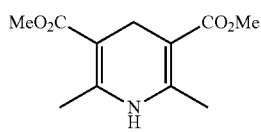

Hantzsch ester b

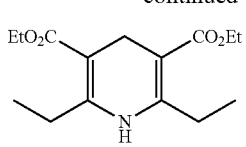

Hantzsch ester c

Such reducing agents can be used alone or in a combination of two or more.

In the reaction of step A, an acid-removing agent, such as amine, can be optionally used.

When compound (4) is used, it is preferable not to use other amines.

When the reducing agent is used in step A, the amount of the reducing agent is preferably within 0.5 to 10 moles, more preferably 1.0 to 5.0 moles, and even more preferably 1.2 to 3.0 moles, per mole of the compound represented by formula (2), which is a substrate.

The reaction of step A can be performed in the presence of a catalyst or in the substantial or complete absence of a catalyst.

The reaction of step A is preferably performed in the presence of a catalyst.

Examples of the catalyst used in the present disclosure include transition metal complexes and organic dye compounds.

Examples of the kinds of central metal contained in the transition metal complexes that can be used in the present disclosure include cobalt, ruthenium, rhodium, rhenium, iridium, nickel, palladium, osmium, and platinum.

Preferable examples of the kinds of central metal include ruthenium, iridium, and palladium.

Examples of ligands of the transition metal complexes that can be used in the present disclosure include nitrogen-containing compounds, oxygen-containing compounds, and sulfur-containing compounds.

Examples of "nitrogen-containing compounds" used as ligands include diamine compounds (e.g., ethylenediamine) and nitrogen-containing heterocyclic compounds (e.g., pyridine, bipyridine, phenanthroline, pyrrole, indole, carbazole, imidazole, pyrazole, quinoline, isoquinoline, acridine, pyridazine, pyrimidine, pyrazine, phthalazine, quinazoline, and quinoxaline.)

Examples of "oxygen-containing compounds" used as ligands include diketones (e.g., dipivaloyl methane) and oxygen-containing heterocyclic compounds (e.g., furan, benzofuran, oxazol, pyran, pyrone, coumarin, and benzopyrone).

Examples of "sulfur-containing compounds" used as ligands include sulfur-containing heterocyclic compounds (e.g., thiophene, thionaphthene, and thiazole).

In the transition metal complex, the number of ligands of these compounds can be one or more. However, needless to say, the number of ligands may not necessarily be clear.

When a catalyst is used in the reaction of step A, the amount of the catalyst in step A is preferably within 0.0001 to 0.1 moles, more preferably 0.001 to 0.05 moles, and even more preferably 0.005 to 0.02 moles, per mole of compound (2).

The organic dye compound that can be used in the present disclosure can be a compound containing no metal atom in the molecule.

Examples of such organic dye compounds include rose bengal, erythrosine, eosine (e.g., eosine B and cosine Y), acriflavine, riboflavine, and thionine.

Preferable examples of catalysts include [Ir{dF(CF$_3$)ppy}$_2$(dtbpY)]PF$_6$, [Ir(dtbbPY)(PIDY)$_2$][PF$_6$], Ir(PPY)$_3$, Ru(bpY)$_3$Cl$_2$·6H$_2$O, [Ru(bpz)$_3$][PF$_6$]$_2$, [Ru(bpm)$_3$][Cl]$_2$, [Ru(bpy)$_2$(phen-5-NH$_2$)][PE$_6$]$_2$, [Ru(bpy)$_3$][PF$_6$]$_2$, Ru(phen)$_3$Cl$_2$, Cu(dap)$_2$ chloride, 9-mesityl-10-methyl acridiniumperchlorate, Ir(ppy)$_3$, and Pd(PPh$_3$)$_4$.

The catalysts can be used alone or in a combination of two or more.

A photoredox catalyst can be preferably used as the catalyst used in step A.

The catalyst used in step A may be carried by a carrier (e.g., zeolite).

The reaction of step A can be performed in the presence of a solvent or in the substantial or complete absence of a solvent.

The reaction of step A is preferably performed in the presence of a solvent.

Examples of solvents used in the present disclosure include dimethylformamide (DMF), toluene, CH$_3$CN, ether, tetrahydrofuran (THF), benzene, dimethylsulfoxide (DMSO), hexane, and benzotrifluoride (BTF).

These solvents can be used alone or in a combination of two or more.

When the reaction of step A starts, the concentration of compound (2) in the mixture of the reaction system is preferably within 1 to 10000 mM, more preferably within 10 to 1000 mM, and even more preferably within 50 to 200 mM.

When the reaction of step A starts, the concentration of compound (3) in the mixture of the reaction system is preferably within 50 to 50000 mM, more preferably within 100 to 5000 mM, and even more preferably within 300 to 1000 mM.

When the catalyst is used in the reaction of step A, the concentration of the catalyst in the mixture of the reaction system is preferably within 0.01 to 100 mM, more preferably within 0.1 to 50 mM, and even more preferably within 0.5 to 20 mM.

Step A can be performed by mixing compound (2) and compound (3) with, as desired, a reducing agent, a catalyst, and a solvent.

Conventional methods can be used for the mixing.

In the mixing, all of the substances can be simultaneously mixed, or sequentially or gradually mixed.

The reaction of step A is performed under light irradiation.

Any irradiation light can be used for light irradiation as long as light can start and/or promote the reaction of step A. Examples of the light source include a low-pressure, medium-pressure, or high-pressure mercury-vapor lamp, tungsten lamp, and light-emitting diode (LED).

The irradiation light can be preferably visible light.

The irradiation light is preferably light having a wavelength of 300 to 600 nm, and more preferably light having a wavelength of 400 to 500 nm.

The irradiation time is preferably within 1 to 24 hours, and more preferably within 10 to 18 hours.

The light irradiation can start before, during, at the same time as, or after mixing.

The intensity of light irradiation may be such that energy for starting and/or promoting the reaction of step A is supplied. For example, the intensity of light irradiation can be suitably adjusted by adjusting, based on common technical knowledge, the output of the light source, the distance between the light source and the reaction system of step A, etc. so that the reaction of step A suitably proceeds.

The reaction of step A can be performed in the presence of an inert gas. Examples of the inert gas include nitrogen and argon.

The reaction temperature in step A is preferably within 0 to 120° C., more preferably within 10 to 80° C., and even more preferably within 20 to 60° C.

When the reaction temperature is within the above ranges, the reaction of step A sufficiently proceeds.

The reaction temperature being within the above ranges is advantageous in view of costs, and undesirable side reaction is inhibited.

The reaction time in step A is preferably within 1 to 24 hours, more preferably within 5 to 18 hours, and even more preferably within 10 to 15 hours.

When the reaction time is within the above ranges, the reaction of step A sufficiently proceeds.

The reaction time being within the above ranges is advantageous in view of costs, and undesirable side reaction is inhibited.

The reaction of step A can be preferably performed in batches or in a flow system.

Compound (1) obtained by the production method of the present disclosure can be purified as desired by a known purification method, such as solvent extraction, drying, filtration, distillation, concentration, and a combination thereof.

According to the production method of the present disclosure, the inversion rate of compound (2), which is a starting material, is preferably 40% or more, more preferably 60% or more, and even more preferably 80% or more.

According to the production method of the present disclosure, the selectivity of compound (1) is preferably 70% or more, and more preferably 80% or more.

According to the production method of the present disclosure, the yield of compound (1) is preferably 40% or more, and more preferably 60% or more.

Compound (1) obtained by the production method of the present disclosure can be used, for example, as a pharmaceutical intermediate.

Production Method: Compound (1a)

The present specification discloses a method for producing a compound represented by formula (1a):

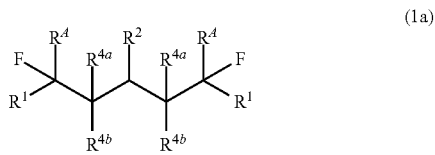

(1a)

wherein $R^1$ independently represents, in each occurrence, an organic group, $R^4$ independently represents, in each occurrence, hydrogen or fluorine, $R^{4a}$ independently represents, in each occurrence, hydrogen or an organic group, and $R^{4b}$ independently represents, in each occurrence, hydrogen or an organic group, and $R^2$ represents hydrogen or an organic group;

the method comprising step Aa of reacting a compound represented by formula (2):

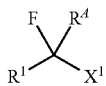

(2)

wherein $X^1$ represents a leaving group, and other symbols are as defined above,
with a compound represented by formula (3):

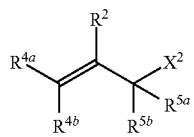

(3)

wherein $X^2$ represents a leaving group, and other symbols are as defined above,
in the presence of a reducing agent as desired, under light irradiation.

Step Aa is the same as step A, except that the product to be produced is different.

In other words, compound (1) and/or compound (1a) can be produced using the substrate and the conditions of the reaction of step A (or step Aa).

Accordingly, step Aa can be understood based on the explanation of step A.

Here, in order to produce compound (Aa) more preferentially, it is preferable to set the amount of compound (3) to be smaller than the amount of compound (2).

Specifically, in this case, the molar ratio of compound (3) to compound (2) can be preferably in the range of 0.9 to 0.1, and more preferably in the range of 0.5 to 0.2.

In contrast, in order to produce compound (A) more preferentially, it is preferable to set the amount of compound (3) to be larger than the amount of compound (2).

Specifically, in this case, the molar ratio of compound (3) to compound (2) can be preferably in the range of 1.1 to 10, and more preferably in the range of 2 to 5.

Compound (1)

This specification also discloses the following compound (which is sometimes referred to as "compound (1)").

A compound represented by formula (1):

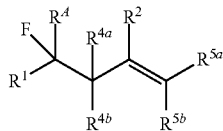

(1)

wherein $R^1$ represents an organic group, represents hydrogen or fluorine,
$R^{4a}$ represents hydrogen or an organic group,
$R^{4b}$ represents hydrogen or an organic group,
$R^2$ represents hydrogen or an organic group,
$R^{5a}$ represents hydrogen or an organic group, and
$R^{3b}$ represents hydrogen or an organic group, with the proviso that
when $R^1$ represents a perfluoroalkyl group, $R^2$ represents an alkyl group having two or more carbon atoms, or an ester group having three or more carbon atoms).

Embodiment 1a1

In compound (1), it is preferable that
$R^1$ represents $R^{11}$—Y— and
Y represents a bond,
$R^{11}$ represents an aryl group that may have one or more substituents, or an alkyl group that may have one or more substituents,
$R^A$ represents hydrogen or fluorine, and
$R^2$ represents hydrogen or an organic group.

$R^{11}$ preferably represents an aryl group or a perfluoroalkyl group.

$R^{11}$ more preferably represents a $C_{6-10}$ aryl group or a $C_{1-10}$ perfluoroalkyl group.

$R^A$ preferably represents fluorine.

$R^2$ preferably represents
hydrogen,
a hydrocarbon group that may have one or more substituents, or
an alkoxycarbonyl group that may have one or more substituents.

$R^2$ more preferably represents
hydrogen,
an alkoxycarbonyl group that may have one or more substituents,
an aryl group that may have one or more substituents, or
an alkyl group that may have one or more substituents $R^2$ more preferably represents
hydrogen,
a $C_{1-6}$ alkyl group that may have one or more substituents,
a $C_{6-14}$ aryl group that may have one or more substituents, or
a $C_{1-6}$ alkoxy-carbonyl group that may have one or more substituents.

$R^2$ is even more preferably hydrogen, a $C_{1-6}$ alkyl group, a $C_{6-14}$ aryl group, or a $C_{1-6}$ alkoxy-carbonyl group.

$R^{4a}$ preferably represents hydrogen.
$R^{4b}$ preferably represents hydrogen.
$R^{5a}$ preferably represents hydrogen.
$R^{5b}$ preferably represents hydrogen.

It is preferable that
$R^{4a}$ represents hydrogen or an organic group;
$R^{4b}$ represents hydrogen or an organic group;
$R^2$ represents hydrogen, an alkoxycarbonyl group that may have one or more substituents, an aryl group that may have one or more substituents, or an alkyl group that may have one or more substituents;
$R^{5a}$ represents hydrogen; and
$R^{5b}$ represents hydrogen.

Embodiment 1a2

In compound (1), it is preferable that
R represents $R^{11}$—Y—;
Y represents —O—C(=O)— or —O—C(=S)—;
$R^{11}$ represents an aliphatic hydrocarbon group that may have one or more substituents;
$R^A$ represents hydrogen or fluorine; and
$R^2$ represents hydrogen or an organic group.

It is preferable that $R^A$ represents fluorine.

It is preferable that $R^2$ represents hydrogen, an alkoxycarbonyl group that may have one or more substituents, an aryl group that may have one or more substituents, or an alkyl group that may have one or more substituents.

It is preferable that $R^2$ represents hydrogen, a $C_{1-6}$ alkoxy-carbonyl group that may have one or more substituents, a $C_{6-14}$ aryl group that may have one or more substituents, or
a $C_{1-6}$ alkyl group that may have one or more substituents.
$R^{4a}$ preferably represents hydrogen.
$R^{4b}$ preferably represents hydrogen.
$R^{5a}$ preferably represents hydrogen.
$R^{5b}$ preferably represents hydrogen.
It is preferable that
$R^{4a}$ represents hydrogen,
$R^{4b}$ represents hydrogen,
$R^2$ represents hydrogen, an alkoxycarbonyl group that may have one or more substituents, an aryl group that may have one or more substituents, or an alkyl group that may have one or more substituents,
$R^{5a}$ represents hydrogen, and
$R^{5b}$ represents hydrogen.

Embodiment 1a3

In compound (I), it is preferable that
$R^1$ represents $R^{11}$—Y—,
Y represents —O—C(=O)— or —O—C(=S)—,
$R^{11}$ represents an aliphatic hydrocarbon group that may have one or more substituents,
$R^A$ represents hydrogen or fluorine, and
$R^2$ represents hydrogen or an organic group.

Embodiment 1a4

In compound (1), it is preferable that
$R^1$ represents $(R^{11}—)_2N—C(=O)—$,
$R^{11}$ independently represents, in each occurrence, an aliphatic hydrocarbon group that may have one or more substituents,
$R^A$ represents hydrogen or fluorine, and
$R^2$ represents hydrogen or an organic group.
It is preferable that $R^{11}$ independently represents, in each occurrence, $C_{1-6}$ alkyl.
$R^A$ preferably represents fluorine.
Production Method: Production Method of Compound (1B)

The present specification further discloses a method for producing a compound (which is sometimes referred to in this specification as "compound (1B)") represented by formula (1B):

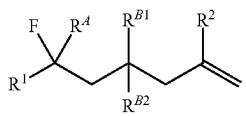

(1B)

wherein
$R^1$ represents an organic group,
$R^A$ represents hydrogen or fluorine,
$R^{B1}$ represents hydrogen or an organic group,
$R^{B2}$ represents hydrogen or an organic group, and
$R^2$ represents hydrogen or an organic group;
the method comprising step $A^2$ of reacting a compound represented by formula (2):

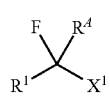

(2)

wherein $X^1$ represents a leaving group, and other symbols are as defined above,
with a compound represented by formula (3):

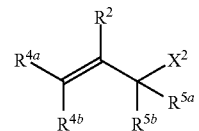

(3)

wherein $X^2$ represents a leaving group, and other symbols are as defined above, and a compound represented by formula (4):

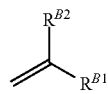

(4)

wherein the symbols are as defined above,
in the presence of a reducing agent under light irradiation.

The amount of compound (4) used in step $A^B$ is in the range of 3 to 20 moles, more preferably in the range of 4 to 15 moles, and even more preferably in the range of 5 to 12 moles, per mole of compound (2).

The other conditions and method of step $A^B$ can be the same as the conditions and method of step A. The details are described below.

The reaction of step $A^2$ is performed under light irradiation.

The irradiation light used in the light irradiation is not particularly limited as long as it is light that starts and/or promotes the reaction in step A. Examples of the light source include low-, medium-, or high-pressure mercury lamps, tungsten lamps, and light-emitting diodes (LEDs).

The irradiation light can be preferably visible light.

The irradiation light is preferably light having a wavelength of 300 to 600 nm, and more preferably light having a wavelength of 400 to 500 nm.

The irradiation time is preferably in the range of 1 to 24 hours, and more preferably in the range of 10 to 18 hours. The light irradiation can start before, during, at the same time as, or after mixing.

The intensity of light irradiation may be such that energy for starting and/or promoting the reaction of step $A^B$ is supplied. For example, the intensity of light irradiation can be suitably adjusted by adjusting, based on common technical knowledge, the output of the light source, the distance between the light source and the reaction system of step $A^B$, etc. so that the reaction of step $A^B$ suitably proceeds.

The reaction of step $A^B$ can be performed in the presence of an inert gas. Examples of the inert gas include nitrogen and argon.

The reaction temperature in step $A^B$ is preferably within 0 to 120° C., more preferably within 10 to 80° C., and even more preferably within 20 to 60° C.

When the reaction temperature is within the above ranges, the reaction of the step $A^B$ sufficiently proceeds.

The reaction temperature being within the above ranges, is advantageous in view of costs, and undesired side effects can be reduced.

The reaction time in step $A^B$ is preferably within 1 to 24 hours, more preferably within 5 to 18 hours, and even more preferably within 10 to 15 hours.

When the reaction time is within the above ranges, the reaction of step $A^B$ sufficiently proceeds.

The reaction time being within the above ranges, it is advantageous in view of costs, and undesired side effects can be reduced.

The reaction of step $A^B$ can be preferably performed in batches or in a flow system.

Compound (1B) obtained by the production method of the present disclosure can be purified, as desired, by a known purification method, such as solvent extraction, drying, filtration, distillation, concentration, and a combination thereof.

According to the production method of the present disclosure, the inversion rate of compound (2), which is a starting material, is preferably 40% or more, more preferably 60% or more, and even more preferably 80% or more.

According to the production method of the present disclosure, the selectivity of compound (1B) is preferably 70% or more, and more preferably 80% or more.

According to the production method of the present disclosure, the yield of compound (1B) is preferably 40% or more, and more preferably 60% or more.

Compound (1B) obtained by the production method of the present disclosure can be used, for example, as a phaLmaceutical intermediate.

EXAMPLES

The present invention is detailed below with reference to Examples; however, the present invention is not limited to these.

The following abbreviations may be used in this specification.
HEH: Hantzsch ester
TTMSS: Tris(trimethylsilyl)silane
DIEA: N,N-diisopropyl ethylamine
bpy: 2,2'-bipyridine In the Examples below, yields are isolated yields unless otherwise specified.

Example 1

Production of Compounds 3a and 4a Under Various Conditions

Using the materials and conditions in Table 1, a solution (solvent: 3 ml) containing compound 1a (0.5 mmol), compound 2a (1.5 or 3.0 equivalents), Hantzsch ester a (HEM), and amine (2 equivalents) was subjected to light irradiation in a glass tube in the presence of a catalyst (1 mol %) using a white LED lamp (5 W) for 12 hours.

As a result, compound 3a and/or compound 4a was obtained in the NMR yields shown in Table 1.

TABLE 1

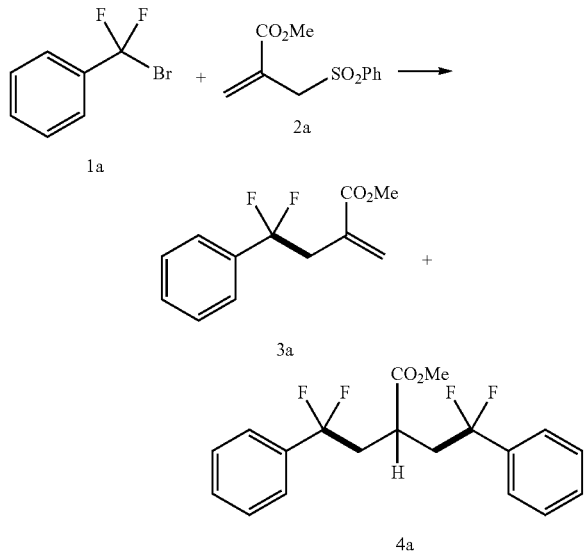

| entry | Catalyst (cat) | Reducing agent (equiv) | Amine | 2a (equiv) | Solvent | 3a (%) | 4a (%) |
|---|---|---|---|---|---|---|---|
| 1 | RuCl$_2$(bpy)$_3$•6H$_2$O | HEH (1.2) | Et$_3$N | 1.5 | DMF | 51 | 21 |
| 2 | Ir(ppy)$_3$ | HEH (1.2) | Et$_3$N | 1.5 | DMF | 20 | 20 |
| 3 | RuCl$_2$(bpy)$_3$•6H$_2$O | TTMSS (1.2) | Et$_3$N | 1.5 | DMF | 13 | 0 |
| 4 | RuCl$_2$(bpy)$_3$•6H$_2$O | NaBH$_3$CN (1.2) | Et$_3$N | 1.5 | DMF | 25 | 28 |
| 5 | RuCl$_2$(bpy)$_3$•6H$_2$O | HEH (0.6) | Et$_3$N | 1.5 | DMF | 49 | 21 |
| 6 | RuCl$_2$(bpy)$_3$•6H$_2$O | HEH (0.6) | DBU | 1.5 | DMF | 0 | 9 |
| 7 | RuCl$_2$(bpy)$_3$•6H$_2$O | HEH (0.6) | DIEA | 1.5 | DMF | 68 | 20 |
| 8 | RuCl$_2$(bpy)$_3$•6H$_2$O | HEH (0.6) | DIEA | 1.5 | CH$_2$Cl$_2$ | 50 | 7 |
| 9 | RuCl$_2$(bpy)$_3$•6H$_2$O | HEH (0.6) | DIEA | 1.5 | MeCN | 68 | 21 |
| 10 | RuCl$_2$(bpy)$_3$•6H$_2$O | HEH (0.6) | DIEA | 2.0 | MeCN | 82 | 12 |
| 11 | RuCl$_2$(bpy)$_3$•6H$_2$O | HEH (0.6) | DIEA | 3.0 | MeCN | 91 | 9 |
| 12[c] | RuCl$_2$(bpy)$_3$•6H$_2$O | HEH (0.6) | DIEA | 3.0 | MeCN | 97 | 3 |
| 13[c] | None | HEH (0.6) | DIEA | 3.0 | MeCN | 0 | 0 |

TABLE 1-continued

[Reaction scheme: compound 1a (PhCF₂Br) + compound 2a (CH₂=C(CO₂Me)CH₂SO₂Ph) → compound 3a (PhCF₂CH₂C(=CH₂)CO₂Me) + compound 4a (bis-adduct with two PhCF₂CH₂ groups on a central CH(CO₂Me))]

| entry | Catalyst (cat) | Reducing agent (equiv) | Amine | 2a (equiv) | Solvent | 3a (%) | 4a (%) |
|---|---|---|---|---|---|---|---|
| 14[c] | RuCl₂(bpy)₃•6H₂O | None | DIEA | 3.0 | MeCN | 53 | 3 |
| 15[c] | RuCl₂(bpy)₃•6H₂O | HEH (0.6) | None | 3.0 | MeCN | 14 | 0 |

Example 2

Production of Allyl Compound Using Difluoro Halo Alkyl Compound and Allyl Sulfone Compound with Ru-Photoreduction Catalyst Using the materials and conditions in Table 2, a DMF solution containing compound 1, compound 2, Ru(bpy)₃Cl₂·6H₂O (1 mol %), ester a (HEH), and Et₃N were subjected to light irradiation in a grass tube using a white LED lamp (5 W) for 2 hours.

As a result, compound 3 was obtained in the yield shown in Table 2. (Symbol c indicates the NMR yield in the table.)

TABLE 2

[General scheme: R¹CF₂Br (1) + CH₂=C(R²)CH₂SO₂Ph (2) → R¹CF₂CH₂C(=CH₂)R² (3); conditions: White LED (5 W), Ru(bpy)₃Cl₂ (1 mol %), HEH, DIEA, MeCN, 2 h]

| entry | 1 | 2 | 3 | yield (%) |
|---|---|---|---|---|
| 1 | 1a (PhCF₂Br) | 2a (CH₂=C(CO₂Me)CH₂SO₂Ph) | 3a (PhCF₂CH₂C(=CH₂)CO₂Me) | 94 |
| 2 | | 2b (CH₂=C(Ph)CH₂SO₂Ph) | 3b (PhCF₂CH₂C(=CH₂)Ph) | 80 |

TABLE 2-continued

| entry | 1 | 2 | 3 | yield (%) |
|---|---|---|---|---|
| 3[b] | | 2c | | 3c 68 |
| 4 | 1b | 2a | | 3d 72 |
| 5 | | 2b | | 3e 72 |
| 6 | | 2d | | 3f 34 (59)[c] |
| 7 | 1c | 2a | | 3g 57 |
| 8 | | 2c | | 3h 47 |
| 9 | | 2d | | 3i 60 |
| 10 | 1d | 2a | | 3j 78 |
| 11 | | 2d | | 3k 74 |

TABLE 2-continued

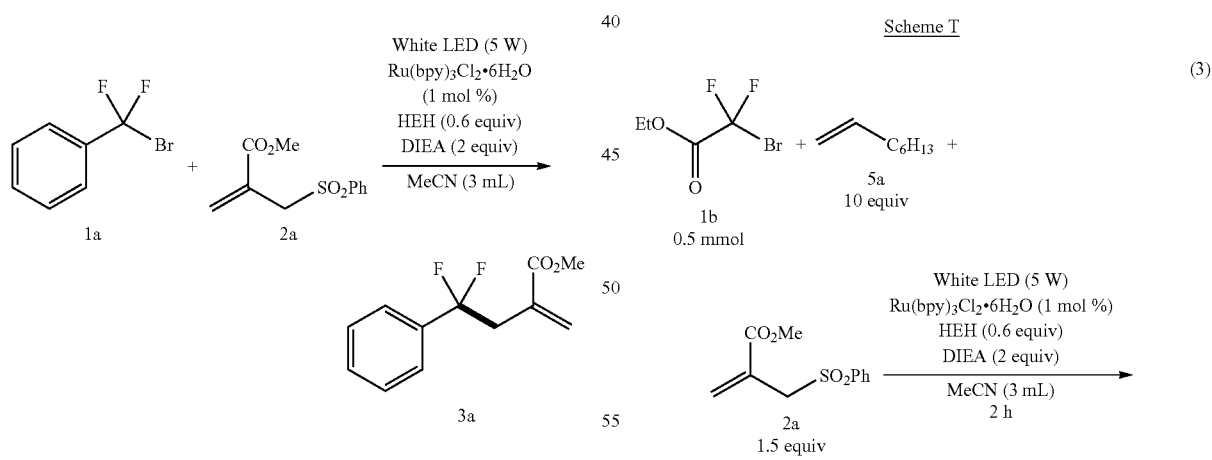

| entry | 1 | 2 | 3 | yield (%) |
|---|---|---|---|---|
| 12 | 1a (C₉F₁₉-CF₂-Br) | 2a | 3l (C₉F₁₉-CF₂-CH₂-C(=CH₂)-CO₂Me) | 31 / 45 |
| 13 | 1e | 2d | 3m (C₉F₁₉-CF₂-CH₂-C(=CH₂)-Me) | 63 |
| 14 | 1f (EtO-C(=O)-CFH-Br) | 2a | 3n (EtO-C(=O)-CFH-CH₂-C(=CH₂)-CO₂Me) | 72 |
| 15 | 1f | 2b | 3o (EtO-C(=O)-CFH-CH₂-C(=CH₂)-Ph) | 60 |

Example 3: Examination of Effects of Light Irradiation

In order to verify the effect of light irradiation using the reaction under the conditions of the above scheme, light irradiation in this system was turned on and off.

After 10 minutes of light irradiation, product 3a was formed in the yield of 49%.

When the light source was turned off to stop light irradiation, the reaction stopped quickly.

26 hours later, when the light source was turned on to restart light irradiation, the reaction was quickly restarted.

Example 4

Scheme T (3)

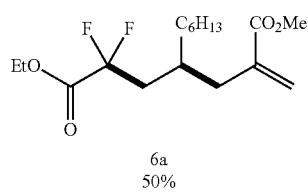

6a
50%

-continued (4)

C$_9$F$_{19}$—CF$_2$—I + 5a (10 equiv) + 2a (1.5 equiv) $\xrightarrow{\begin{array}{c}\text{White LED (5 W)}\\\text{Ru(bpy)}_3\text{Cl}_2\cdot 6\text{H}_2\text{O}\\\text{(1 mol \%)}\\\text{HEH (0.6 equiv)}\\\text{DIEA (2 equiv)}\\\text{MeCN (3 mL)}\\\text{2 h}\end{array}}$ 1c
0.5 mmol C$_9$F$_{19}$—CF$_2$—CH(C$_6$H$_{13}$)—CH$_2$—C(CO$_2$Me)=CH$_2$ 6b
56%

In addition to compounds 1 and 2 in the above Example, the three-component radical reaction was tested in the Example by the addition of alkene(1-octene 5a) under the conditions of Scheme T above.

By the reaction of the three components, i.e., 2-bromo-2,2-difluoroacetic acid ethyl 1b, 1-octene 5a, and 2-methoxycarbonyl-substituted allyl sulfone 2a, product 6a was obtained in a yield of 50%.

By the reaction of the three components, i.e., perfluorodecyl bromide 1e, 1-octene 5a, and 2-phenyl allyl sulfone 2a, compound 6b was obtained in a yield of 56%.

The invention claimed is:

1. A method for producing a compound represented by formula (1):

(1)

[structure showing R$^1$, F, R$^A$, R$^{4a}$, R$^2$, R$^{4b}$, R$^{5b}$, R$^{5a}$]

wherein R$^1$ represents an organic group,
R$^A$ represents hydrogen or fluorine,
R$^{4a}$ represents hydrogen or an organic group,
R$^{4b}$ represents hydrogen or an organic group,
R$^2$ represents hydrogen or an organic group,
R$^{5a}$ represents hydrogen or an organic group, and
R$^{5b}$ represents hydrogen or an organic group; or
R$^2$ is optionally connected to R$^{4a}$ to form a ring;
the method comprising step A of reacting a compound represented by formula (2):

(2)

[structure showing R$^1$, F, R$^A$, X$^1$]

wherein X$^1$ represents a leaving group, and other symbols are as defined above, with a compound represented by formula (3):

(3)

[structure showing R$^{4a}$, R$^2$, R$^{4b}$, R$^{5b}$, R$^{5a}$, X$^2$]

wherein X$^2$ represents a leaving group, and other symbols are as defined above, optionally in the presence of a reducing agent, under light irradiation.

2. The production method according to claim 1, wherein
R$^1$ represents R$^{11}$—Y— or (R$^{11}$—)$_2$N—,
Y represents a bond, and
R$^{11}$ independently represents, in each occurrence, a hydrocarbon group that optionally has one or more substituents.

3. The production method according to claim 2, wherein
R$^1$ represents R$^{11}$—Y—,
Y represents a bond, and
R$^{11}$ represents
an aryl group that optionally has one or more substituents, or
an alkyl group that optionally has one or more substituents.

4. The production method according to claim 2, wherein
R$^1$ represents R$^{11}$—Y—,
Y represents —O—C(=O)— or —O—C(=S)—, and
R$^{11}$ represents an aliphatic hydrocarbon group that optionally has one or more substituents.

5. The production method according to claim 2, wherein
R$^1$ represents (R$^{11}$—)$_2$N—C(=O)— and
R$^{11}$ independently represents, in each occurrence, an aliphatic hydrocarbon group that optionally has one or more substituents.

6. The production method according to claim 1, wherein R$^A$ represents fluorine.

7. The production method according to claim 1, wherein
R$^{4a}$ represents hydrogen,
R$^{4b}$ represents hydrogen,
R$^2$ represents hydrogen, a hydrocarbon group that optionally has one or more substituents, or an alkoxycarbonyl group that optionally has one or more substituents,
R$^{5a}$ represents hydrogen, and
R$^{5b}$ represents hydrogen.

8. The production method according to claim 1, wherein X$^1$ represents halogen, an alkylsulfonyloxy group, or an arylsulfonyloxy group.

9. The production method according to claim 1, wherein X$^2$ represents
—SO$_2$R,
—SR,
—S(=O)R,
—SeR,
—TeR,
—Cl,
—Br,
—I,
—PR$_2$, or
—P(=O)R$_2$,
wherein R independently represents, in each occurrence, an organic group.

10. The production method according to claim 9, wherein $X^2$ represents —$SO_2R$, wherein R is an organic group.

11. The production method according to claim 1, wherein the reducing agent is a nitrogen-containing unsaturated heterocyclic compound having an N—H moiety.

12. The production method according to claim 1, wherein the reducing agent is a compound represented by formula (4):

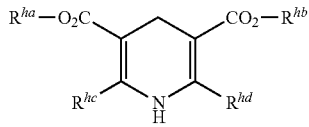

wherein $R^{ha}$, $R^{hb}$ and $R^{hd}$ are the same or different, and each represents alkyl.

13. The production method according to claim 1, wherein the reaction of step A is performed in the presence of a catalyst.

14. The production method according to claim 13, wherein the catalyst is at least one member selected from the group consisting of a transition metal complex and an organic dye compound.

15. A method for producing a compound represented by formula (1a):

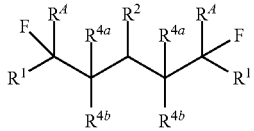

(1a)

wherein $R^1$ independently represents, in each occurrence, an organic group, $R^A$ independently represents, in each occurrence, hydrogen or fluorine, $R^{4a}$ independently represents, in each occurrence, hydrogen or an organic group, $R^{4b}$ independently represents, in each occurrence, hydrogen or an organic group, and $R^2$ represents hydrogen or an organic group;

the method comprising step Aa of reacting a compound represented by formula (2):

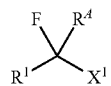

(2)

wherein $X^1$ represents a leaving group, and other symbols are as defined above, with a compound represented by formula (3):

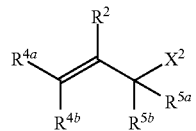

(3)

wherein $X^2$ represents a leaving group, and other symbols are as defined above, optionally in the presence of a reducing agent, under light irradiation.

* * * * *